United States Patent
Bonda et al.

(10) Patent No.: US 6,355,261 B1
(45) Date of Patent: Mar. 12, 2002

(54) ULTRAVIOLET RADIATION ABSORBING WAXES USEFUL IN COSMETIC COMPOSITIONS

(75) Inventors: Craig A. Bonda, Wheaton; Urvil B. Shah, Mokena; Peter J. Marinelli, Barlett, all of IL (US)

(73) Assignee: The C. P. Hall Company, Bedford Park, IL (US)

(*) Notice: Subject to any disclaimer, the term of this patent is extended or adjusted under 35 U.S.C. 154(b) by 0 days.

(21) Appl. No.: 09/452,929

(22) Filed: Dec. 2, 1999

(51) Int. Cl.[7] .............. A61K 6/00; A61K 7/00; A61K 7/42; A61K 7/021; A61K 7/025

(52) U.S. Cl. .............. 424/401; 424/59; 424/63; 424/64

(58) Field of Search .............. 424/400, 401, 424/59, 64, 63

(56) References Cited

U.S. PATENT DOCUMENTS

| | | | |
|---|---|---|---|
| 3,937,811 A | 2/1976 | Papantoniou et al. | 424/64 |
| B14,405,641 | 11/1986 | Seibert | 514/785 |
| 4,818,521 A | 4/1989 | Tamabuchi | 424/62 |
| 4,839,161 A | 6/1989 | Bowser et al. | 424/59 |
| 4,885,270 A | 12/1989 | Tsuchiya et al. | 503/209 |
| 4,891,227 A | 1/1990 | Thaman et al. | 424/443 |
| 4,891,228 A | 1/1990 | Thaman et al. | 424/443 |
| 4,970,220 A | * 11/1990 | Chaussee | 514/358 |
| 4,983,382 A | 1/1991 | Wilmott et al. | 424/62 |
| 5,063,050 A | 11/1991 | Verdon et al. | 424/63 |
| 5,104,586 A | 4/1992 | Brand et al. | 514/785 |
| 5,234,682 A | 8/1993 | Macchio et al. | 424/69 |
| 5,262,407 A | * 11/1993 | Leveque et al. | 514/159 |
| 5,308,621 A | 5/1994 | Taylor et al. | 424/401 |

(List continued on next page.)

FOREIGN PATENT DOCUMENTS

| | | |
|---|---|---|
| JP | 52029826 | 3/1977 |
| JP | 60146845 | 8/1985 |
| JP | 63249686 | 10/1988 |
| JP | 04-036238 | 2/1992 |
| JP | 25235896 | 9/1996 |
| WO | WO 93/10755 | 6/1993 |
| WO | WO 93/10756 | 6/1993 |

OTHER PUBLICATIONS

Suranyi et al., "Spectrophotometric Study of the Formation of Iron(III) Complexes with some Salicylic Acid Derivatives", Collect. Czech. Chem. Commun., vol. 60, No. 3, pp. 464–472, 1995.*

(List continued on next page.)

*Primary Examiner*—Thurman K. Page
*Assistant Examiner*—S. Howard
(74) *Attorney, Agent, or Firm*—Marshall, Gerstein & Borun

(57) ABSTRACT

The compounds of formula (I),

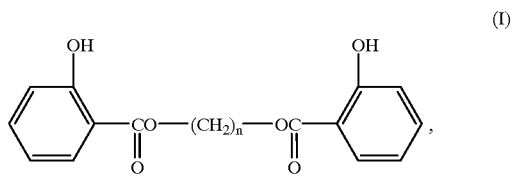

suitable solvents for the compounds, and use of the compounds as waxes, UV absorbers, and skin conditioners is disclosed. A compound of formula (I) is a wax at room temperature, absorbs UVA and UVB radiation, and boosts the sun protection factor of sunscreen compositions. The compounds of formula (I) have utility in a variety of cosmetics and other compositions including waxes for coating, polishing, and sealing, textile and leather manufacture, adhesives, and crafts. The compounds of formula (I) also have utility in the treatment of skin conditions including acne, psoriasis, seborrheic dermatitis, dandruff, warts, corns, calluses, ringworm infection, wrinkling, yellowing, leatheriness, mottling, and hyperpigmentation.

31 Claims, 2 Drawing Sheets

In vitro Analysis of Sunscreens with and without HDDS

U.S. PATENT DOCUMENTS

| | | | |
|---|---|---|---|
| 5,612,021 A | 3/1997 | Mellul | 424/61 |
| 5,614,201 A | 3/1997 | Slavtcheff et al. | 424/401 |
| 5,620,682 A | 4/1997 | Fogel | 424/60 |
| 5,690,918 A | 11/1997 | Jacks et al. | 424/64 |
| 5,728,732 A | 3/1998 | Corey et al. | 514/544 |
| 5,741,497 A * | 4/1998 | Guerrero et al. | 424/401 |
| 5,773,015 A | 6/1998 | Bajor et al. | 424/401 |
| 5,911,974 A | 6/1999 | Brieva et al. | 424/64 |
| 5,939,083 A | 8/1999 | Allec et al. | 424/401 |
| 5,945,090 A | 8/1999 | Randall et al. | 424/59 |
| 5,948,394 A | 9/1999 | Walling et al. | 424/64 |
| 5,997,887 A | 12/1999 | Ha et al. | 424/401 |
| 6,024,969 A | 2/2000 | Agostini et al. | 424/401 |
| 6,083,516 A | 7/2000 | Curtis et al. | 424/401 |
| 6,086,858 A | 7/2000 | McEleney et al. | 424/59 |
| 6,123,952 A | 9/2000 | Lagrange | 424/401 |
| 6,177,093 B1 | 1/2001 | Lombardi et al. | 424/401 |
| 6,180,125 B1 | 1/2001 | Ortiz et al. | 424/401 |
| 6,197,319 B1 | 3/2001 | Wang et al. | 424/401 |
| 6,235,293 B1 | 5/2001 | De La Poterie et al. | 424/401 |

OTHER PUBLICATIONS

J.M. Nikitakis, Ed.; *CTFA Cosmetic Ingredient Handbook*, first edition; pp. 51, 55, 58–59, 61–63, 77–87, 90–94, 98; The Cosmetic, Toiletry and Fragrance Association, Inc.; Washington, D.C. (1988).

The Society of Cosmetic Chemists, course on Color and Make–up; J. Hollenberg and A. Farer; 37 selected unnumbered pages; Newark, NJ (1998).

Roelandts, et al., A Survey of Ultraviolet Absorbers in Commercially Available Sun Products, Intl. J. Derm. 22(4) pp. 247–255 (1983).

CTFA Cosmetic Ingredient Handbook, Section 2, Functions, pp. 51–101, $1^{st}$ Ed. (1988).

CAS Registry No. 62702–44–7.

* cited by examiner

ULTRAVIOLET RADIATION ABSORBING WAXES USEFUL IN COSMETIC COMPOSITIONS

BACKGROUND OF THE INVENTION

1. Field of the Invention

The invention generally relates to a class of salicylic acid esters and, more specifically, the invention relates to a class of diol-disalicylates useful as waxes, including cosmetic waxes, as ultraviolet radiation absorbers, and in the treatment of skin conditions including acne.

2. Brief Description of Related Technology

Cosmetic compositions generally are defined as compositions suitable for application to the human body. Cosmetic compositions such as creams and lotions are used to provide moisture to hair and skin and to keep skin in a smooth, supple condition. Pigmented cosmetic compositions such as makeup, blush, lipstick, and eyeshadow are used to color the skin and lips.

In general, cosmetic emulsions are composed of a fatty phase, an aqueous phase, active materials and, optionally, pigments, preservatives, and ultraviolet radiation filters. Cosmetic compositions can also be anhydrous systems containing waxes, oils, and pigments. In the fatty phase, in addition to emulsifiers, oil components and antioxidants, consistency regulators are employed to increase the viscosity and thus to improve the consistency required for a stable emulsion system. Consistency regulators in water-in-oil emulsions include, for example, beeswax, paraffin, petroleum jelly, microcrystalline waxes, and metal stearates. In oil-in-water emulsions, it is customary to use spermaceti, fatty alcohols, and glycerofatty acid esters.

Waxes are lower-melting organic mixtures or compounds of high molecular weight, solid at room temperature, and generally are similar in composition to fats and oils except that they contain no glycerides. They can be hydrocarbons or esters of fatty acids and alcohols. Waxes generally can be categorized as animal waxes, vegetable waxes, mineral waxes, natural waxes, synthetic waxes, petroleum waxes, ethylenic polymers, hydrocarbons such as Fischer-Tropsch waxes, silicone waxes, and mixtures thereof Natural waxes traditionally used in cosmetic compositions include waxes of animal origin, e.g., beeswax, spermaceti, and lanolin (wool wax); waxes of vegetable origin, e.g. candelilla, carnauba, bayberry, and sugarcane wax; waxes of mineral origin, e.g. ceresin, montan, and ozokerite; and waxes of petroleum origin, e.g. paraffin and microcrystalline wax. Animal, plant, and some mineral waxes are primarily esters of a high molecular weight fatty alcohol with a high molecular weight fatty acid.

Synthetic waxes include long chained polymers of ethylene oxide combined with a dihydric alcohol, namely polyoxyethylene glycol, (including carbowax), hydrocarbon waxes derived from carbon monoxide and hydrogen (Fischer-Tropsch synthesis waxes), and silicone waxes such as methyloctadecane-oxypolysiloxane and poly (dimethylsiloxy)stearoxysiloxane.

Cosmetic waxes have an emollient effect on the skin, giving a film permeable for moisture (i.e. water vapor) and gas. Cosmetic waxes have, and impart, desired characteristics to a cosmetic composition such as structure, body, or hardness (e.g. in lipid-based materials such as lipsticks and hair pomades), high viscosity (e.g. to emulsions and suspensions), spreadability, long wear, and stability. Typically, cosmetic waxes will have a melting point in the range of about 32° C. to about 120° C.

Candelilla, a typical cosmetic wax, has a melting point of about 70° C. Most waxes having a melting point of about 70° C. provide structure and hardness, but have a waxy, tacky, or grabby feel. Cosmetic compositions made with traditional cosmetic waxes may be prone to oil breakthrough, creasing, ruboff, and difficulty adhering to pigments. In addition, some natural waxes, such as beeswax, are in increasingly short supply. Synthetic waxes, although useful in some cosmetic applications, can also have undesirable tactile or compositional characteristics and also may be costly to produce.

Beta-hydroxy acids (BHA's) also have been used in cosmetic compositions. BHA's include salicylic and citric acids, derivatives of salicylic acid, and their salts. BHA's are lipid soluble and penetrate to the thicker dermal skin layers located below the epidermis. BHA's are effective in exfoliating the lower dermal skin layers, which results in increased cell turnover and the production of new skin cells. It is known that salicylic acid esters and salicylic acid derivative esters, such as tridecyl salicylate, are broken down by esterases in human skin, releasing salicylic acid. It is also known that salicylic acid derivatives and their esters are effective in controlling, reducing and inhibiting oil and grease production by skin. Thus, BHA's are useful in the treatment of adult acne, reversing the effects of premature skin aging, reducing thin lines and wrinkles, and producing firmer, smoother-looking skin.

PCT applications WO 93/10755 and WO 93/10756 report salicylic acid as an effective anti-wrinkling agent. U.S. Pat. No. 5,262,407 reports use of ring acylated salicylic acid as a treatment against skin aging. Salicylic acid has also been described for the treatment of acne in U.S. Pat. Nos. 4,891,227 and 4,891,228. Moreover, salicylic acid has been used for the removal of warts, corns, and calluses; for the treatment of psoriasis, seborrheic dermatitis, and dandruff; and for the topical treatment of ringworm infection.

Sunscreen agents also have been used in cosmetic compositions. Lengthy exposure of the skin to ultraviolet (UV) light typically damages the skin, resulting in sunburn, photoaging, and carcinogeneses. The results of photodamage may be identical to those of aging except that they appear at an accelerated rate. Wriniding, yellowing, leatheriness, mottling, and hyperpigmentation are also associated with sun damage. UV light exposure in the presence of oxygen results in the creation of free radicals. In the skin, these radicals frequently trigger the release of inflammatory mediators, commonly manifested as sun burn, cytoskeletal alterations, breakdown of collagen in the skin, and may also result in structural DNA changes, such as DNA strand breaks and dimer formation.

Sunscreen agents and sunscreen formulations for use on human skin are widely used and are available for diverse consumer needs. Different agents and formulations give different Sun Protection Factor (SPF) values, from 2–4 ("minimal" protection), 4–6 ("moderate" protection), 8–15 ("maximum" protection), and above 15 to indicate "ultra" sun protection.

Sunscreen components include dioxybenzone (benzophenone-8), ethylhexyl p-methoxycinnamate (octyl methoxycinnamate), 2-ethylhexyl salicylate (octyl salicylate), oxybenzone (benzophenone-3), titanium dioxide, p-aminobenzoic acid (PABA) and PABA derivatives. Various other sunscreen materials are found in "A Survey of Ultraviolet Absorbers in Commercially Available Sun Products," by Roelandts, et al., International Journal of Dermatology, Vol. 22, pages 247–55 (May 1985). Sunscreen compositions can also include a diester and/or polyester of a naphthalene dicarboxylic acid that photostabilizes sunscreen components.

Traditional sunscreen compositions for use on human skin are liquids, solids that require solvation, or particulate solids such as metal oxides. Incorporation of a sunscreen composition into a traditional cosmetic composition affects the physical characteristics of the cosmetic composition and creates obstacles to achieving desirable formulations. For example, incorporation of a liquid sunscreen composition, or a solid sunscreen composition in solution, lowers the viscosity and melting point of a cosmetic composition. As another example, metal oxide particulates, such as titanium dioxide, are difficult to maintain within a wax system due to their tendency to migrate out of the wax system.

Ultraviolet (UV) radiation absorbers also have been used in cosmetic compositions to protect the product from chemical or physical deterioration induced by ultraviolet light. UV absorbers, like sunscreen agents, have the ability to convert incident ultraviolet radiation into less damaging infrared radiation (heat). UV absorbers include allantoin PABA, butyl methoxydibenzoylmethane, ethyl diisopropylcinnamate, octyl methoxycinnamate, octyl salicylate, and PABA Various other UV absorbers can be found in the CTFA Cosmetic Ingredient Handbook, J. M. Nikitakis, Ed., 1st Edition (1988).

Accordingly, a continuing need exists for compounds useful in cosmetic compositions which provide desirable structure, viscosity, and tactile characteristics. It would also be desirable to have compounds useful in cosmetic compositions which are useful in the treatment of skin conditions such as adult acne, improving the firmness and smoothness of skin, and protecting skin from the damaging effects of ultraviolet radiation.

SUMMARY OF THE INVENTION

In brief, the invention generally is a class of salicylic acid esters and, more specifically, the invention is a class of diol-disalicylates useful as waxes, including cosmetic waxes, as ultraviolet radiation absorbers, and in the treatment of skin conditions including acne.

Accordingly, one aspect of the invention is a compound of formula (I)

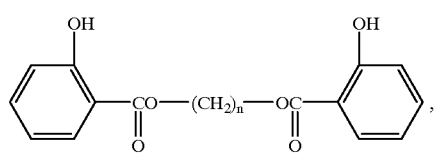

(I)

wherein n is an integer from 3 to 12, preferably an integer 4 to 12, more preferably an integer 4 to 8, most preferably 6.

Another aspect of the invention is a composition including a compound of formula (I) and a solvent including an ester of a $C_{3\text{-}10}$ dibasic acid, preferably selected from the group consisting of diisopropyl sebacate, diisopropyl adipate, dioctyl maleate, dioctyl adipate, diethylhexyl naphthalate, and mixtures thereof.

Another aspect of the invention is a wax composition including a compound of formula (I) and a cosmetically useful material.

Yet another aspect of the invention is a cosmetic composition including a compound of formula (I) and a cosmetically useful material.

Still another aspect of the invention is a sunscreen composition including a compound of formula (1) and at least one of a sunscreen agent and an ultraviolet light absorber.

Another aspect of the invention is to provide a method of protecting skin from ultraviolet radiation including topically applying to the skin a compound of formula (I) in a cosmetically acceptable carrier, preferably with at least one of a sunscreen agent and an ultraviolet light absorber.

A further aspect of the invention is to provide a method of treating skin conditions selected from the group consisting of acne, psoriasis, seborrheic dermatitis, dandruff, warts, corns, calluses, ringworm infection, wrinkling, yellowing, leatheriness, mottling, and hyperpigmentation, the method including topically applying to the skin a safe and effective amount of a compound of formula (I), preferably in a cosmetically acceptable carrier, most preferably in a pharmaceutically acceptable carrier.

An additional aspect of the invention is to provide a method of increasing the sun protection factor of a sunscreen composition including adding a compound of formula (I) to the sunscreen.

Still another aspect of the invention is to provide a process for preparing a compound of formula (I), wherein n is an integer 3 to 12, including reacting salicylic acid with a $C_3$–$C_{12}$ diol.

Another aspect of the invention is to provide cosmetic compositions, including pressed face powder, loose face powder, pressed face foundation, blush, eyeshadow, anhydrous foundation, anhydrous mascara, anhydrous eyeshadow, glossy classic lipstick, matte classic lipstick, and volatile lipstick, that generally include about 0.01 wt. % to about 50 wt. % of a compound of formula (I).

Further aspects and advantages of the invention may become apparent to those skilled in the art from a review of the following detailed description, taken in conjunction with the appended claims. It should be noted, however, that while the invention is susceptible of embodiments in various forms, described hereinafter are specific embodiments of the invention with the understanding that the present disclosure is intended as illustrative, and is not intended to limit the invention to the specific embodiments described herein.

DETAILED DESCRIPTION OF THE PREFERRED EMBODIMENTS

Figure 1:
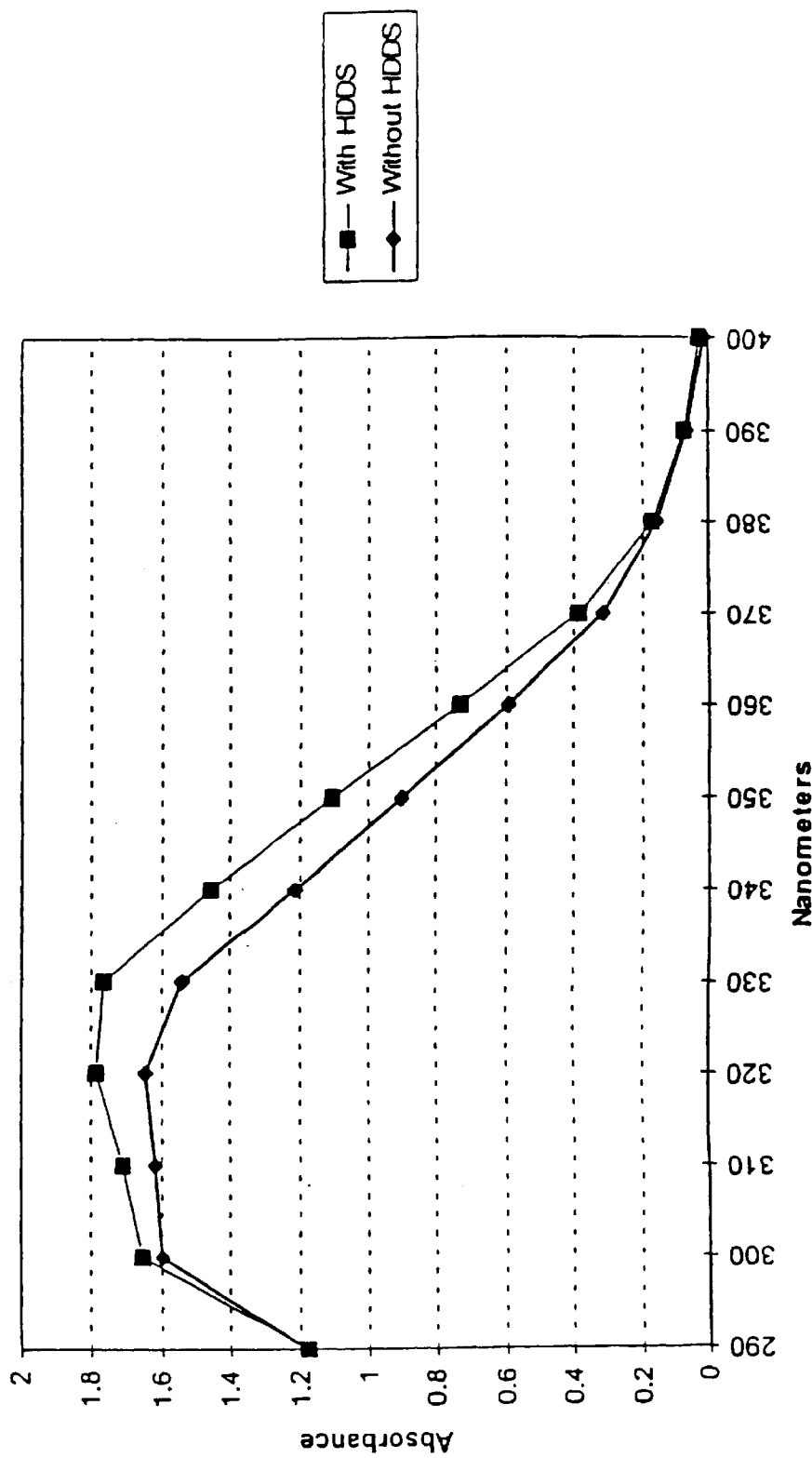
FIG. 1 is an overlay plot comparing UV radiation transmittance of a control sunscreen composition and a sunscreen composition in accordance with the invention.

The invention is directed to a class of diol-disalicylates, to the methods of their preparation, to their use as waxes, to cosmetic and pharmaceutical compositions containing them, and to their use as ultraviolet radiation filters.

One aspect of the invention is a class of $C_{3\text{-}12}$diol-disalicylates of the formula (I)

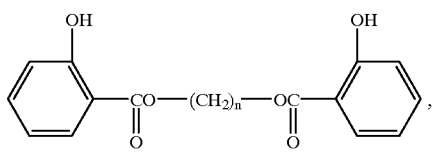

(I)

wherein n is an integer 3 to 12, preferably 4 to 12, more preferably 4 to 8, for example 6. Particular individual compounds of the invention include hexanediol disalicylate (HDDS) and octanediol disalicylate. The invention also includes mixtures of the compounds of formula (I).

It has been shown that the compounds of formula (I) have melting points comparable to those of conventional natural and synthetic waxes. The compounds of the invention also have excellent emollient properties, spreadability, moisture permeability, structure and hardness, adhesion to pigment, stability, long wear, and a dry, non-oily, silky, tactile feel. Thus, the compounds of formula (I) are of interest for use in any application where conventional waxes are used, particularly in cosmetic compositions.

Suitable solvents for use with the compounds of formula (I) include, but are not limited to, esters of $C_{3-10}$ dibasic acids. Preferably, solvents for use with the compounds of formula (I) include an ester of a $C_{3-10}$ dibasic acid selected from the group consisting of adipic acid, azelaric acid, glutaric acid, maleic acid, malic acid, malonic acid, naphthalic acid, phthalic acid, succinic acid, and mixtures thereof.

In particular, applications of the compounds of formula (I) include, but are not limited to, use as binders, emulsion stabilizers, viscosity increasing agents, hair conditioning agents, hair fixatives, emollients, skin conditioning agents, ultraviolet light absorbers, and consistency regulators.

The compounds of formula (I) preferably may be combined with cosmetically useful materials to form cosmetic compositions of the invention. Cosmetically useful materials include, but are not limited to, antioxidants, binders, bulking agents, chelating agents, colorants, emollients, emulsion stabilizers, film formers, fillers, fragrance components, gelling agents, hair conditioning agents, hair fixatives, humectants, plasticizers, preservatives, skin conditioning agents, solvents, sunscreen agents, surfactants, ultraviolet light absorbers, viscosity controlling agents, and waxes. Various other cosmetically useful materials can be found in the CTFA Cosmetic Ingredient Handbook, J. M. Nikitakis, Ed., 1st Edition, pages 51–101 (1988), the disclosure of which is hereby incorporated herein by reference.

Cosmetic compositions of the invention include cosmetic compositions that can contain a wax, including, but not limited to, blushers, creams (including face creams, hand creams, moisturizing creams, and sunscreen creams), cream powders, eye liners, eye shadows, eyebrow pencils, foundations, gels (including face gels, hand gels, moisturizing gels, and sunscreen gels), lipsticks, lip balms, lotions (including face lotions, hand lotions, moisturizing lotions, and sunscreen lotions), mascaras, microemulsions, ointments, pomades, and rouges.

A cosmetic composition of the invention includes about 0.01 weight percent (wt. %) to about 50 wt. %, preferably about 0.1 wt. % to about 20 wt. %, more preferably about 0.5 wt. % to about 10 wt. %, even more preferably about 1 wt. % to about 8 wt. % of a compound of formula (I).

According to another aspect of the invention, there is provided the use of a compound of formula (I) in the manufacture of cosmetic compositions.

Another aspect of the invention is a compound and method for imparting desired adhesion to pigment, emorfiency, hardness, long wear, moisture permeability, spreadability, stability, structure, and specific tactile characteristics to a cosmetic composition.

The compounds of formula (I) also may be combined with other waxes, including cosmetic waxes, to tailor the desired characteristics of a wax-containing composition. Thus, another aspect of the invention is a combination of a compound of formula (I) and a wax, including a cosmetic wax.

It has also been shown that the compounds of formula (I) block transmission of, absorb, or filter out ultraviolet (UV) radiation. Thus, a further aspect of the invention is a compound and method for blocking transmission of, absorbing, or filtering out UV radiation.

The compounds of formula (I) also can be blended, layered, or admixed with other materials to impart UV blocking, UV absorbing, or UV filtering characteristics to those materials. Examples of suitable materials include, but are not limited to, other waxes and pigments. Thus, another aspect of the invention is compounds and methods for imparting UV blocking, UV absorbing, or UV filtration characteristics to a material.

In particular, the compounds of formula (I) can be blended into suitable cosmetic compositions to provide protection to human skin against UV light in increased Sun Protection Factor (SPF) levels. Suitable cosmetic compositions include cosmetic compositions that can contain a wax, including, but not limited to, blushers, creams (including face creams, hand creams, moisturizing creams, and sunscreen creams), cream powders, eye liners, eye shadows, eyebrow pencils, foundations, gels (including face gels, hand gels, moisturizing gels, and sunscreen gels), lipsticks, lip balms, lotions (including face lotions, hand lotions, moisturizing lotions, and sunscreen lotions), mascaras, microemulsions, ointments, pomades, and rouges. Thus, another aspect of the invention provides UV absorbing cosmetic compositions for protecting human skin against UV radiation. A UV absorbing cosmetic composition of the invention includes about 0.01 wt. % to about 50 wt. %, preferably about 0.1 wt. % to about 20 wt. %, more preferably about 0.5 wt. % to about 10 wt. %, even more preferably about 1 wt. % to about 8 wt. % of a compound of formula (I).

The compounds of formula (I) also can be used in combination with traditional sunscreen compositions or UV absorbers to provide enhanced levels of UV protection and higher SPF values of compositions for use on human skin. Suitable sunscreen compositions for use on human skin are known to those in the art and include, but are not limited to, octyl methoxycinnamate, benzophenone-3, butyl methoxydibenzoylmethane, oxybenzone, PABA and PABA derivatives. Various other sunscreen materials are found in "A Survey of Ultraviolet Absorbers in Commercially Available Sun Products," by Roelandts, et al., International Journal of Dermatology, Vol. 22, pages 247–55 (May 1985) and the CTFA Cosmetic Ingredient Handbook, J. M. Nikitakis, Ed., 1st Edition, pages 86–87 (1988), the disclosures of which are hereby incorporated herein by reference. Sunscreen compositions of the invention can also include a diester and/or polyester of a naphthalene dicarboxylic acid that photostabilizes sunscreen components.

Suitable UV absorbers are known to those in the art and include, but are not limited to, allantoin PABA, butyl methoxydibenzoylmethane, ethyl diisopropylcinnamate, octyl methoxycinnamate, octyl salicylate, and PABA. Various other UV absorbers can be found in the CTFA Cosmetic Ingredient Handbook, J. M. Nikitakis, Ed., 1st Edition, page 98 (1988), the disclosure of which is hereby incorporated herein by reference. Thus, another aspect of the invention is a sunscreen composition comprising a compound of formula (I) and at least one of a sunscreen agent and an ultraviolet light absorber. A sunscreen composition of the invention includes about 0.01 wt. % to about 50 wt. %, preferably about 0.1 wt. % to about 20 wt. %, more preferably about 0.5 wt. % to about 10 wt. %, even more preferably about 1 wt. % to about 8 wt. % of a compound of formula (I).

The compounds of formula (I) also are of interest for use in non-cosmetic compositions comprising a wax in which ultraviolet light filtration or specific tactile characteristics are desired. Examples include waxes for coating, polishing and sealing (such as for automobiles, boats, floors, fruits and vegetables, furniture, and paper), textile and leather manufacture, adhesives, and crafts.

The compounds of formula (I) also are useful in the treatment of skin conditions including acne, psoriasis, seborrheic dermatitis, dandruff, warts, calluses, ringworm infection, wrinkling, yellowing, leatheriness, mottling, and hyperpigmentation. Because the compounds of formula (I) are themselves emollients, they may be topically applied either with or without a cosmetically acceptable carrier, including a pharmaceutically acceptable carrier. The carrier, when used, can be aqueous, anhydrous, or an emulsion, including an organic solvent.

When used as a treatment for skin conditions, a compound of formula (I) preferably will be delivered in a safe and effective amount. The term "safe and effective amount" is defined as any amount sufficient to induce a positive modification in the condition to be treated, but low enough to avoid serious side effects (at a reasonable benefit/risk ratio), within the scope of sound medical judgement. The safe and effective amount of the compounds of formula (I) will vary with the particular condition being treated, the age and physical condition of the patient being treated, the severity of the condition, the duration of the treatment, the nature of concurrent therapy, the specific compound or compounds of the invention being employed, the particular carrier used, if any, and similar factors in the knowledge and expertise of the attending physician. Generally, these amounts will be in a range of about 0.01 wt. % to about 50 wt. %, preferably about 0.1 wt. % to about 20 wt. %, more preferably about 0.5 wt. % to about 10 wt. %, even more preferably about 1 wt. % to about 8 wt. %, optimally about 2 wt. % to about 6 wt. %.

Cosmetic compositions according to the invention will now be described. In one class of embodiments, a compound of formula (I) can be incorporated into cosmetic powders, including, but not limited to, pressed face powder, loose face powder, pressed face foundation, blush, and eyeshadow.

Generally, cosmetic powder embodiments of the invention will have the following compositions of ingredients, by weight %.

| | Pressed Face Powder | Loose Face Powder | Pressed Face Foundation | Blush | Eye Shadow |
|---|---|---|---|---|---|
| fillers | 30–70 | 40–90 | 40–80 | 30–70 | 30–60 |
| compression aides | 3–5.0 | 0–2.5 | 2–4.0 | 2–5.0 | 3–7.0 |
| texture enhancers | 10–40 | 10–40 | 10–30 | 10–40 | 3–30 |
| colorants | 2–10 | 2–10 | 1–10 | 2–10 | 1–25 |

-continued

| | Pressed Face Powder | Loose Face Powder | Pressed Face Foundation | Blush | Eye Shadow |
|---|---|---|---|---|---|
| pearls | 0–10 | 10–20 | — | 10–20 | 0–50 |
| liquid binder | 3–8.0 | 2–4.0 | 4–8.0 | 3–10 | 3–15 |
| additional raw ingredients | QS | QS | QS | QS | QS |

In cosmetic powder embodiments of the invention, fillers include, but are not limited to, talc, mica (including wet ground and dry ground), sericite, starches, flours, and magnesium carbonate. Compression aides include, but are not limited to, fatty soaps (including lithium stearate/laurate, zinc stearate/palmitate/myristate, magnesium stearate/myristate, and aluminum stearate), kaolin, calcium silicate, polyethylene, press aides (including synthetic waxes and corn gluten protein), and tribehenin/tripalmitin.

Texture enhancers include, but are not limited to, nylon, lauroyl lysine, boron nitride, polyethylene, polypropylene, ethylene acrylates co-polymer, powdered natural waxes, PMMA, silica beads, bismuth oxychloride, composite powders (including nylon/mica, silica/mica, and lauroyl lysine/mica), teflon, teflon composites, polyurethane powders, silicone powders, glass beads, polyvinylidene co-polymer, acrylates co-polymer, and microcrystalline cellulose.

Colorants include, but are not limited to, titanium dioxide (including pigmentary and ultrafine), iron oxides (including pigmentary and ultrafine), organic colorants, zinc oxide (including pigmentary and ultrafine), ultramarines, magnesium violet, ferrous blue, chromium greens, carmine, and pearlescent pigments (commonly referred to as "pearls"). Pearlescent pigments include guanine, bismuth oxychloride, mica, titanium dioxide coated mica, and iron oxide coated mica.

A liquid binder includes, but is not limited to, a combination of oils, esters, waxes, emulsifiers, silicones, and polymers (including polydecenes, permethyls, and polybutenes).

Additional raw ingredients include, but are not limited to, light diffusers (including barium sulfatelmica, ultrafine titanium dioxide/PMMA, ultrafine titanium dioxide/mica, and silica/mica), clays, classic silicas, hydrophobic silicas, sunscreens, emulsifiers, and actives.

Cosmetic powder compositions of the invention include about 0.01 wt. % to about 50 wt. %, preferably about 0.1 wt. % to about 20 wt. %, more preferably about 0.5 wt. % to about 10 wt. %, even more preferably about 1 wt. % to about 8 wt. % of a compound of formula (I). Preferably, a compound of formula (I) is included in the composition in place of, or in addition to, one or more traditional compounds, most preferably compounds classified as compression aides, texture enhancers, liquid binders, and additional raw ingredients. In a cosmetic powder composition of the invention, a compound of formula (I) provides creaminess, aids in compression and adhesion, enhances pick-up and deposit, enhances water-resistance, develops colorants, provides UV absorption, and improves skin conditions including acne and wrinkling.

The cosmetic powder compositions of the invention described above can be prepared by any suitable method known in the art, or by the following process which forms part of the present invention. A powder phase including fillers, colorants, compression aids, and texture enhancers is added to a suitable high shear mixer and mixed until uniform, or is passed through a micro pulverizer equipped with a screen having a size about 0.01 inches to about 0.027 inches, until the colorants are completely extended and the phase is uniform. Pearls are then added, and the resulting powder phase is mixed thoroughly with mild shear. Next, a liquid binder is added slowly as a fine mist into the powder phase with high shear agitation to provide a uniform deposit of the binder onto the powders, or the powder phase and liquid binder together are passed through a micro pulverizer equipped with a screen having a size about 0.25 inches until the phase is uniform.

In another class of embodiments, a compound of formula (I) can be incorporated into anhydrous cosmetic compositions, including, but not limited to, anhydrous foundations, anhydrous mascaras, and anhydrous eyeshadows.

Generally, an anhydrous foundation embodiment of the invention will have the following composition of ingredients, by weight %.

| Anhydrous Foundation | |
| --- | --- |
| emollients (including fluids, low melting point waxes, and gel-like raws) | 30–60 |
| waxes | 5–10 |
| wetting agents | 0.50–1.00 |
| colorants | QS |
| texturizing agents | 30–60 |

In an anhydrous foundation embodiment of the invention, emollients preferably are texturally light and of low viscosity. Emollients include, but are not limited to, oils, esters, and silicones.

Waxes include, but are not limited to, natural waxes (including beeswax, jojoba, carnuaba, orange, candelilla, and castor), beeswax derivatives (including siliconyl, cera bellina, butyl-octanyl, hexanediol-behenyl), synthetic waxes (including paraffins, microcrystalline waxes, polyethylene, and highly branched olefin polymers), fatty alcohols and fatty alcohol ethoxylates (including unithox and unilin), fatty esters (including SYNCROWAX waxes and KESTER waxes).

Wetting agents include, but are not limited to, low HLB emulsifiers, polyglyceryl esters (including polyglyceryl-3 diisostearate), hydrogentated lecithin, lanolin alcohols, polyhydroxystearic acid, and soya sterols.

Texturizing agents in an anhydrous foundation of the invention preferably are surface treated. Texturizing agents include, but are not limited to, nylon, PMMA, serecite, talc, mica, boron nitride, teflon, microbubbles (including glass and polyvinylidene), spherical silica, starches (including oat, rice, wheat, and corn), bismuth oxychloride, microcrystalline cellulose, polyurethane powder, and silicone powder.

Pigments preferably are surface treated and include, but are not limited to, titanium dioxide (including pigmentary and ultrafine), zinc oxide (including pigmentary and ultrafine), and iron oxides (including pigmentary and ultrafine).

Surface treated raw materials are preferred in these embodiments to improve dispersibility and enhance solids loading to provide a a drier texture, create a matte appearance, and improve wear.

Anhydrous foundation compositions of the invention include about 0.01 wt. % to about 50 wt. %, preferably about 0.1 wt. % to about 20 wt. %, more preferably about 0.5 wt. % to about 10 wt. %, even more preferably about 1 wt. % to about 8 wt. % of a compound of formula (I). Preferably, a compound of formula (I) is included in the composition in place of, or in addition to, one or more traditional compounds, most preferably compounds classified as emollients and waxes. In an anyhdrous foundation composition of the invention, a compound of formula (I) provides creaminess, aids in adhesion, enhances water-resistance, develops colorants, provides UV absorption, and improves skin conditions including acne and wrinkling.

The anhydrous foundation composition of the invention described above can be prepared by any suitable method known in the art, or by the following process which forms part of the present invention. Emollients, waxes, and wetting agents are introduced into a jacketed kettle and heated until the phase is clear and uniform. Pigments and texturizing agents are slowly introduced into the oil phase with high shear mixing, and mixing is continued until dispersion is uniform and colorants are completely extended.

Generally, anhydrous mascara and eyeshadow embodiments of the invention will have the following compositions of ingredients, by weight %.

| | Anhydrous Mascara | Anhydrous Eyeshadow |
| --- | --- | --- |
| volatile solvents | 40–60 | 35–55 |
| waxes | 10–20 | 7–12 |
| emollients | — | 3–8 |
| resins | 3–10 | — |
| gellants | 3–7 | 1.5–3.5 |
| colorants/pearls | 5–15 | 5–20 |
| fillers | — | 10–20 |
| functional fillers | 2–10 | 5–15 |

In anhydrous mascara and eyeshadow embodiments of the invention, volatile solvents include, but are not limited to, hydrocarbons (including SHELLSOL 71 hydrocarbons and isododecane), isoparaffinic hydrocarbons (isoparaffins), and volatile silicones (including cyclomethicone, hexamethyldisiloxane, and alkyl silicones).

Waxes include, but are not limited to, beeswax and its derivatives, candelilla, carnauba, parafin, polyethylene, microcrystalline waxes, castor, synthetic waxes, ceresin, and ozokerite.

Emollients include, but are not limited to, esters, oils, and silicones.

Resins, when used, include, but are not limited to, aromatic/aliphatic resins, hydrogenated aromatic resins, polyterpene, synthetic resins (including pentaerythrityl hydrogenated rosinate), rosin, acrylics, silicones, and other resins (including polyol prepolymers and LEXOREZ 100 resins, sold by Inolex Corporation).

Gellants include, but are not limited to, clays (including stearalkonium hectorite, quaternium-18 bentonite, and quaternium-18 hectorite), and metal soaps (including aluminum and zinc stearates).

Colorants and pearls preferably include a classic raw material without any surface treatment.

Fillers include, but are not limited to, mica, talc, and sericite.

Functional fillers include, but are not limited to, spherical particles (including PMMA, silica, nylon, and microbubbles), boron nitride, starches, silica, lauroyl lysine, and teflon.

Anhydrous mascara and eyeshadow compositions of the invention preferably include about 0.01 wt. % to about 20 wt. %, more preferably about 0.5 wt. % to about 10 wt. %, even more preferably about 1 wt. % to about 8 wt. % of a compound of formula (I). Preferably, a compound of formula (I) is included in the composition in place of, or in addition to, one or more traditional compounds, most preferably compounds classified as emollients and waxes. In anhydrous mascara and eyeshadow compositions of the invention, a compound of formula (I) provides body to enhance thickening, improves deposit, enhances water-resistance, develops colorants, provides UV absorption, and improves skin conditions including acne and wrinkling.

The anhydrous mascara and eyeshadow compositions of the invention described above can be prepared by any suitable method known in the art, or by the following process which forms part of the present invention. Heat the waxes, solvents, and emollients or resins, when used, in a jacketed kettle until the mixture is uniform and clear. Slowly add colorants next under high shear and mill until the dispersion is uniform. Next, under high shear, add gellants and mill until uniform, then activate gellants with a polar material (such as propylene carbonate). Under high shear, add fillers and functional fillers, and mill until uniform, then cool to the desired temperature.

In another embodiment, a compound of formula (I) can be incorporated into lipstick compositions including, but not limited to, classic lipsticks (including glossy and matte lipsticks), and volatile lipsticks. Generally, classic lipstick embodiments of the invention will have the following compositions of ingredients, by weight %.

| Classic Lipstick | | |
| --- | --- | --- |
|  | Glossy | Matte |
| emollients | 50–70 | 40–55 |
| waxes | 10–15 | 8–13 |
| plasticizers | 2–5 | 2–4 |
| colorants | 0.5–3.0 | 3.0–8.0 |
| pearl | 1–4 | 3–6 |
| actives | 0–2 | 0–2 |
| fillers | 1–3 | 4–15 |
| fragrance | 0.05–0.10 | 0.05–0.10 |
| preservatives/antioxidates | about 0.5 | about 0.5 |

In a classic lipstick embodiment of the invention, emollients include, but are not limited to, castor oil, esters, lanolin/lanolin oil, oily alcohols (including octyl dodecanol), organically modified silicones (including phenyltrimethicone, and aillyl dimethicones), meadowfoam seed oil, jojoba oil and esters, and triglycerides.

Waxes include, but are not limited to, candelilla, carnauba, beeswax and derivatives, microcrystalline wax, ozokerite, cerisine, alkyl silicones, castor, polyethylenes, lanolin, paraffins, synthetic waxes, and esters.

Plasticizers work in conjunction with the waxes to improve texture, application, and stability of the lipsticks. Plasticizers include, but are not limited to, cetyl acetate and acetylated lanolin, oleyl alcohol, synthetic lanolin, acetylated lanolin alcohol, and petrolatum.

Colorants include, but are not limited to, D & C's (including Red #6 and Ba Lake, Red #7 and Ca Lake, Red #21 and Al Lake, Red #27 and Al Lake, Red #33 and Al Lake, Red #30, Red #36, and Yellow #10), F D & C's (including Yellow #5 and 6 and Al Lake; Blue #1 and Al Lake), iron oxides, titanium dioxide, zinc oxide, and pearls. Generally, Fe Blue, ultramarines, and magnesium violet should be avoided.

Actives include, but are not limited to, tocopheryl acetate, sodium hyaluronate, aloe extract, ascorbyl palmitate, silinols (including biosil and exsymol), ceramides, panthenol, amino acids, and beta carotene.

Fillers include, but are not limited to, mica, silicas (including classic and spherical), nylon, PMMA, teflon, boron nitride, bismuth oxychloride, starches, lauroyl lysine, composite powders, and acrylates co-polymers.

Preservatives/antioxidates include, but are not limited to, BHA, BHT, rosemary extract, citric acid, propyl paraben, and methyl paraben.

Classic lipstick compositions of the invention include about 0.01 wt. % to about 50 wt. %, preferably about 0.1 wt. % to about 20 wt. %, more preferably about 0.5 wt. % to about 10 wt. %, even more preferably about 1 wt. % to about 8 wt. % of a compound of formula (I). Preferably, a compound of formula (I) is included in the composition in place of, or in addition to, one or more traditional compounds, most preferably compounds classified as emollients and waxes. In classic lipstick compositions of the invention, a compound of formula (I) provides enhanced water-resistance, UV absorption, structure, body, hardness, adhesion to pigment, stability, long wear, and a silky tactile feel.

The classic lipstick compositions of the invention described above can be prepared by any suitable method known in the art, or by the following process which forms part of the present invention. Pigments are pre-milled either in an emollient or in the complete emollient phase, either by a 3-roller mill, stone mill, or a type of ball mill. The grind phase is added to the complete emollient phase and waxes, and heated and mixed until uniform (about 90° C. to about 105° C.). Pearls and fillers are added to the above phases and mixed with shear (if necessary) until homogenous. Next, add the actives, preservatives, fragrance, and antioxidants and mix until uniform. Finally, hold the temperature of the mixture above the initial set point of the waxes, and fill as appropriate.

Generally, volatile lipstick embodiments of the invention will have the following compositions of ingredients, by weight %.

| Volatile Lipstick | |
| --- | --- |
| solvents | 25–60 |
| emollients | 1–30 |
| waxes | 10–25 |
| fixatives | 1–10 |
| fillers | 1–15 |
| colorants/pearls | 1–15 |
| fragrance | 0.05–0.10 |

Solvents include, but are not limited to, isododecane, alkyl silicones, and cyclomethicone.

Emollients include, but are not limited to, phenyl trimethicone, esters, alkyl silicones (including fluids and pastes), and vegetable or plant oil.

Waxes include, but are not limited to, polyethylene, synthetic waxes, ceresin, ozokerite, paraffin, beeswax, and alkyl silicones.

Fixatives include, but are not limited to, silicone resins, including dilsostearyl trimethyl propate siloxy silicate and dilauryl trimethyl propane siloxy silicate.

Generally, the colorants, pearls, actives, and fillers useful in volatile lipstick compositions are identical to those useful in classic lipstick compositions Volatile lipstick compositions of the invention include about 0.01 wt. % to about 50 wt. %, preferably about 0.1 wt. % to about 20 wt. %, more preferably about 0.5 wt. % to about 10 wt. %, even more preferably about 1 wt. % to about 8 wt. % of a compound of formula (I). Preferably, a compound of formula (I) is included in the composition in place of, or in addition to, one or more traditional compounds, most preferably compounds classified as emollients and waxes. In volatile lipstick compositions of the invention, a compound of formula (I) provides enhanced water-resistance, UV absorption, structure, body, hardness, adhesion to piglnent, stability, long wear, and a silky tactile feel.

The volatile lipstick compositions of the invention described above can be prepared by any suitable method known in the art, or by the following process which forms part of the present invention. Pigments are pre-milled either in an emollient or in the complete emollient phase, either by a 3-roller mill, stone mill, or a type of ball mill. The grind phase is added to the complete emollient phase, solvent, and waxes in a closed vessel to prevent loss of volatile components. The mixture is heated and mixed until uniform (about 90° C. to about 105° C.). Pearls and fillers are added to the above phases and mixed with shear (if necessary) until homogenous. Next, add the fragrance and fixatives and mix until uniform. Finally, hold the temperature of the mixture above the initial set point of the waxes, and fill as appropriate.

Compounds of formula (I) may be prepared by any suitable method known in the art or by the following process which forms part of the present invention. In the method below, n is an integer 3 to 12, unless otherwise indicated.

Thus, a process for preparing a compound of formula (I) generally comprises reacting salicylic acid with a $C_{3-12}$glycol in the presence of a catalyst such as methane sulfonic acid (MSA) and an antioxidant such as sodium hypophosphate. Preferably, the glycol is added at up to about 10% molar equivalent excess, more preferably up to about 5%, for example 5%. A catalyst such as MSA preferably is added in a range of about 0.01 wt. % to about 0.4 wt. % of the glycol and salicylic acid reactants, more preferably about 0.1 wt. % to about 0.3 wt. %, for example 0.2 wt. %. An antioxidant such as sodium hypophosphate preferably is added in a range of about 0.001 wt. % to about 0.1 wt. % of the glycol and salicylic acid reactants, more preferably about 0.01 wt. % to about 0.07 wt. %, for example 0.03 wt. %.

EXAMPLES

The following examples are provided to illustrate the invention but are not intended to limit the scope of the invention.

Example 1

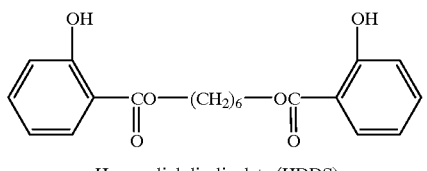

Hexanediol disalicylate (HDDS)

To a 2-liter, 3-neck, glass flask sequentially was added salicylic acid powder (1035 g), 1,6-hexanediol (melted, 465 g), sodium hypophosphite (0.45 g), and MSA (3 g in 50% solution with water). The resulting mixture was heated to 350° F. with agitation and under nitrogen gas flow (5 cfm) until the acid value (by ASTM D1613) was less than 5.0, about 25 hours. The product then was cooled to about 170° F. to about 180° F. and neutralized with sodium hydroxide solution to an acid value less than about 1. The product then was washed twice with a 20% sodium sulfate wash and steam stripped. Steam stripping was accomplished by raising the temperature of the mixture to about 230° F., applying a full (about 40 mm Hg) vacuum, and injecting steam for about 40 minutes. The resulting product was dried under vacuum for about 15 minutes, and cooled to about 160° F. to 170° F. The product was filtered with ½ wt. % CELITE brand filter aid, available from Celite Corporation of Lompoc, Calif., to yield a white solid having an APHA color value of 81 (ASTM D1209), acid value of 0.10, saponification value (4 hours) of 297.4, melting point of 69–71° C., and a water content of 0.03 wt. %. Based on the theoretical saponification value of 313.4, the resulting HDDS was about 95% pure.

HDDS was found to be soluble in diisopropyl adipate, dilsopropyl sebacate, dioctyl maleate, dioctyl adipate, and dioctyl sebacate at least 5% by weight.

Example 2

| | Oil in Water Foundation | | | |
|---|---|---|---|---|
| Ingredients | Preferred Brand | Supplier | Function | wt. % |
| Water Phase Ingredients | | | | |
| deionized water | | | solvent | 50.98 |
| dimethicone copolyol | SILSOFT L-7087 | Witco | emollient | 0.10 |
| 80% titanium dioxide/talc | | | pigment | 9.00 |
| 80% yellow iron oxide/talc | | | pigment | 0.80 |
| 80% red iron oxide/talc | | | pigment | 0.45 |
| 80% black iron oxide/talc | | | pigment | 0.08 |
| talc | MICROACE P-2 | Presperse | texturizig agent | 1.67 |
| sodium dihydroxy cetyl phosphate, isopropyl hydroxycetyl ether | DRAGOPHOS S | Dragoco | emulsifier | 1.50 |
| propylene glycol | | | humectant, solvent | 4.00 |
| magnesium aluminum silicate | VEEGUM Regular | Vanderbilt | thickener | 1.00 |
| propylene glycol | | | humectant, solvent | 4.00 |
| cellulose gum | CMC 7H3SF | Aqualon | thickener | 0.14 |

-continued

Oil in Water Foundation

| Ingredients | Preferred Brand | Supplier | Function | wt. % |
|---|---|---|---|---|
| sucrose cocoate | CRODESTA SL-40 | Croda | emollient | 1.50 |
| methyl paraben | | | preservative | 0.20 |
| disodium EDTA | | | chelating agent | 0.05 |
| Oil Phase Ingredients | | | | |
| propylene glycol dicaprylate/dicaprate | NEOBEE M-20 | Stepan | emollient | 12.00 |
| cetyl alcohol | ALFOL 16 | Vista | wax | 0.75 |
| sorbitan monolaurate | ARLACEL 20 | ICI | emulsifier | 2.50 |
| HDDS | | | wax, UV absorber, skin conditioner | 2.00 |
| propyl paraben | | | preservative | 0.10 |
| cyclomethicone ($D_5$) | | | emollient | 6.00 |
| Miscellaneous | | | | |
| deionized water | | | solvent | 1.00 |
| DMDM hydantoin | | | preservative | 0.18 |

Combine oil phase, heating to 75° C. to 80° C. with stirring. Combine water and dimethicone copolyol. Begin homomixing, moderate speed, and heating to 70° C. while adding pigments. When no undispersed color remains, add sodium dihydroxy cetyl phosphate and isopropyl hydroxycetyl ether. Combine magnesium aluminum silicate and propylene glycol. Add to batch. Heat to 85° C. to 90° C. for 15 minutes while homomixing. Cool to 75° C. to 80° C. Combine and add cellulose gum and propylene glycol. Add remaining water phase ingredients in order. Add cyclomethicone to oil phase. Adjust oil phase temperature to 77° C. to 80° C. and water phase temperature to 72° C. to 77° C. Add oil to water while homomixing. Maintain temperature and agitation for 15 minutes. Cool to 45° C. with paddle mixer agitation. Combine and add DMDM hydantoin and water. Cool to 30° C. Drop batch.

Example 3

Moisturizing Lipstick

| Ingredients | Preferred Brand | Supplier | Function | wt. % |
|---|---|---|---|---|
| Color Grinds | | | | |
| 35% D&C Red#6 Ba Lake/castor oil | | | colorant | 4.30 |
| 35% D&C Red#7 Ca Lake/castor oil | | | colorant | 4.30 |
| Waxes, Oils, and Parabens | | | | |
| castor oil | | | emollient | 41.00 |
| candellila | | | wax | 5.00 |
| carnauba | | | wax | 2.20 |
| ceresin | OZOKERITE 170D | Ross | wax | 1.80 |
| microcrystalline wax | MICROWAX 214 | Ross | wax | 3.50 |
| HDDS | | | wax, UV absorber, skin conditioner | 4.00 |
| isostearyl stearoyl stearate | HETESTER ISS | Bernel | occlusive | 6.00 |
| caprylic/capric triglyceride | NEOBEE M-5 | Stepan | emollient | 18.50 |
| octyldodecanol | EUTANOL G | Henkel | emollient, solvent | 6.00 |
| hydroxylated lanolin | OHLAN | Amerchol | emollient | 1.00 |
| methyl paraben | | | preservative | 0.20 |
| propyl paraben | | | preservative | 0.10 |
| Miscellaneous | | | | |
| mica | SILK MICA | Rona | filler, colorant, texturizing agent | 2.00 |
| ascorbyl palmitate | | | antioxidant | 0.10 |

Premill the color grinds using a three roll mill to <25 μm. Combine waxes, oils, and parabens. Heat to 85° C. to 90° C., with stirring, until clear. Add color grinds and mica, stirring until homogenous. De-air by maintaining agitation for one hour at 75° C. to 80° C. (or apply vacuum). Add ascorbyl palmitate. Pour at 68° C. to 70° C.

Example 4

| | Cream Powder Makeup | | | |
|---|---|---|---|---|
| Ingredients | Preferred Brand | Supplier | Function | wt. % |
| Waxes, Oils, and Parabens | | | | |
| octyl palmitate | | | emollient | 42.20 |
| glyceryl tribehenate | SYNCROWAX HRC | Croda | wax, oil | 7.00 |
| HDDS | | | wax, UV absorber, skin conditioner | 7.00 |
| polyglyceryl-3 diisostearate | EMEREST 2452 | Henkel | emulsifier, wetting agent | 0.50 |
| methyl paraben | | | preservative | 0.20 |
| propyl paraben | | | preservative | 0.10 |
| Pigments and Fillers | | | | |
| titanium dioxide, octyltriethoxysilane | TITANIUM DIOXIDE AS | Cardre | colorant | 10.00 |
| iron oxides, octyltriethoxysilane | YELLOW IRON OXIDE AS | Cardre | colorant | 0.94 |
| iron oxides, octyltriethoxysilane | RED IRON OXIDE AS | Cardre | colorant | 0.47 |
| iron oxides, octyltriethoxysilane | BLACK IRON OXIDE AS | Cardre | colorant | 0.04 |
| talc, octyltriethoxysilane | TALC AS | Cardre | texturizing agent, colorant | 3.55 |
| mica, octyltriethoxysilane | MICA 8 AS | Cardre | texturizing agent, filler, colorant | 13.00 |
| polymethylmethacrylate, octyltriethoxysilane | PMMA AS | Cardre | texturizing agent | 15.00 |

Combine waxes, oils, and parabens. Heat to 75° C. to 80° C. with stirring, until clear. Add pigments and fillers, stirring until homogenous. Pass over a three roll mill until no undispersed color remains. De-air by maintaining agitation for one hour at 75° C. to 80° C. (or apply vacuum). Pour at 68° C. to 70° C.

Example 5

Sunscreen lotion compositions were made and tested for UV absorbance. A control sample sunscreen lotion was made without a compound of formula (I) and a test sample was made in accordance with the invention, using a compound of formula (I) wherein n is 6 (HDDS). Table 1 summarizes the composition of the control and HDDS sunscreen lotions, by wt. %.

TABLE 1

| | Sunscreen Lotions | | | |
|---|---|---|---|---|
| Phase | Chemical Name | Function | Control | HDDS |
| A | octyl methoxycinnamate | UVB sunscreen | 5.00 | 5.00 |
| A | butyloctyl salicylate | solvent, emollient | 5.00 | 5.00 |
| A | isopropyl myristate | solvent, emollient | 6.00 | 4.00 |
| A | PPG-2 myristyl ether proprionate | solvent | 1.50 | 1.00 |
| A | oxybenzone | UVB/UVA sunscreen | 3.00 | 3.00 |
| B | HDDS | test substance | 0.00 | 2.50 |
| B | polyglyceryl-3 methyl glucose distearate | emulsifier | 2.50 | 2.50 |

TABLE 1-continued

Sunscreen Lotions

| Phase | Chemical Name | Function | Control | HDDS |
|---|---|---|---|---|
| B | $C_{30-38}$ olefin-isopropyl maleate/MA copolymer | waterproofer | 1.00 | 1.00 |
| C | deionized water | carrier, solvent | 68.90 | 68.90 |
| C | disodium EDTA | chelator | 0.05 | 0.05 |
| C | butylene glycol | solvent, humectant | 2.00 | 2.00 |
| C | glycerin | humectant | 4.00 | 4.00 |
| C | phenoxyethanol()methyl-paraben()ethylparaben()propyl-paraben()butylparaben | preservative | 0.70 | 0.70 |
| D | carbomer | stabilizer | 0.20 | 0.20 |
| E | triethanolamine (99%) | neutralizer | 0.15 | 0.15 |

To prepare the sunscreen lotions, the A phase ingredients were blended together and heated to 90° C. to dissolve the oxybenzone. Next, the B phase ingredients were added with stirring until homogeneous. In a separate vessel, EDTA was dissolved in water and heated to 85° C. A preblended mixture of preservative, butylene glycol, and glycerin was added to the EDTA/water solution. In a separate vessel, carbomer was dispersed in 50 g water and set aside. With homogenization, the A+B oil phase was added to the C water phase. Next, the pre-dispersed carbomer D phase was added to the A+B+C mixture. While maintaining the temperature at 85° C., the mixture was homogenized for about 10 minutes, and then removed from heat and stirred with a propellor while cooling. When the temperature was below 40° C., the neutralizer E was slowly added and the mixture was stirred until a smooth, homogeneous lotion resulted.

Ultraviolet radiation transmittance and SPF of the control and HDDS samples were measured over the range 290 to 400 nm using a LABSPHERE Ultraviolet Transmittance Analyzer. Five scans were performed on each sample. Critical Wavelength (nm) and SPF data are reported in Table 2 below for the control and HDDS samples. A summary of transmittance and SPF data is provided in Table 3 below.

TABLE 2

SPF and Critical Wavelength (nm)

| Scan No. | SPF Control | SPF HDDS | Critical Wavelength (nm) Control | Critical Wavelength (nm) HDDS |
|---|---|---|---|---|
| 1 | 20.56 | 23.36 | 357 | 357 |
| 2 | 22.45 | 24.74 | 358 | 359 |
| 3 | 21.26 | 23.34 | 358 | 358 |
| 4 | 19.90 | 26.50 | 357 | 359 |
| 5 | 20.62 | 26.96 | 357 | 359 |

TABLE 3

Transmittance and SPF

| | SPF Control | SPF HDDS | UVA Transmittance % Control | UVA Transmittance % HDDS | UVB Transmittance % Control | UVB Transmittance % HDDS |
|---|---|---|---|---|---|---|
| number of scans | 5 | 5 | 5 | 5 | 5 | 5 |
| mean value | 21.0 | 25.0 | 35.68 | 32.42 | 3.15 | 2.88 |
| standard deviation (%) | 1.0 | 1.7 | 1.23 | 1.51 | 0.12 | 0.28 |
| Coefficient of variation (%) | 4.60 | 6.82 | 3.45 | 4.67 | 3.90 | 9.77 |
| UVA ratio | 0.45 | 0.51 | | | | |

The data reported above show that the presence of HDDS in a sunscreen lotion reduces the transmittance of UVA and UVB radiation. The data also demonstrate that the presence of HDDS in a sunscreen lotion boosts the SPF value of the lotion.

An overlay plot of the control sample (average of five scans) and HDDS (average of five scans) is shown in FIG. 1. The ordinate represents absorbance, in units log(base 10)*(1/transmittance (%)), and the abscissa represents wavelength in nanometers. FIG. 1 shows that the presence of HDDS increases UV absorbance of the lotion at every wavelength of radiation measured.

Example 6

Figure 2:
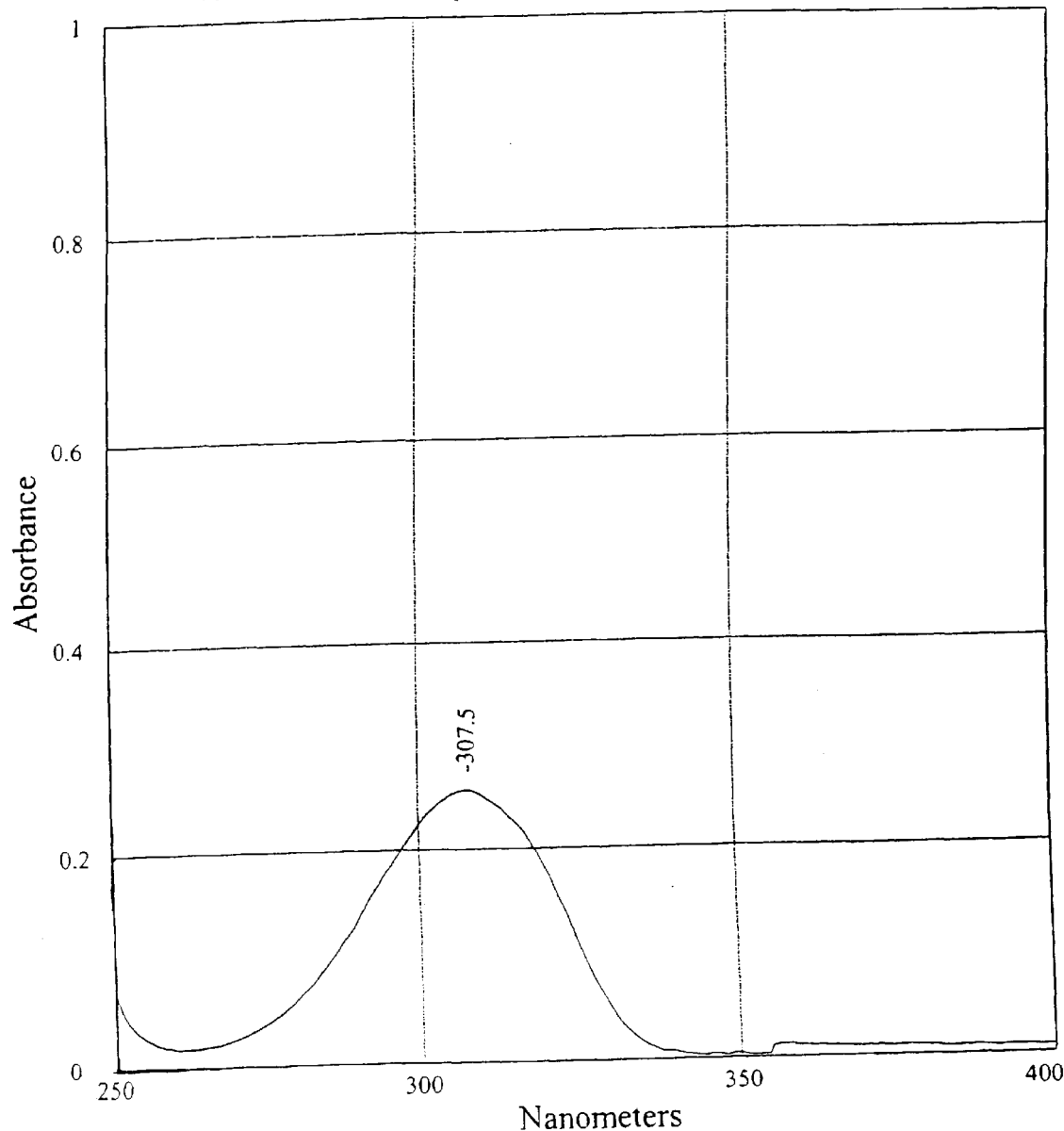
FIG. 2 is a plot showing the UV absorbance of hexanediol disalicylate of Example 1 at 10 ppm in cyclohexane.

The compound of Example 1, HDDS, was dissolved to 10 ppm in cyclohexane. The UV absorbance of the compound was measured over the range 250 nm to 400 nm. FIG. 2 is a graph showing the UV absorbance where 0 is no absorbance and 1 is fill absorbance. The plot is annotated with the wavelength at peak absorbance.

The foregoing description is given for clearness of understanding only, and no unnecessary limitations should be understood therefrom, as modifications within the scope of the invention may be apparent to those having ordinary skill in the art.

What is claimed is:

1. A cosmetic composition comprising a cosmetically useful material and a compound of formula (I), wherein n is 6.

2. A cosmetic composition of claim 1 comprising an emulsion.

3. A composition comprising a compound of formula (I),

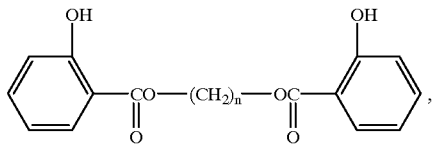

wherein n is an integer 3 to 12, and a solvent comprising an ester of a $C_{3-10}$ dibasic acid.

4. A composition of claim 3 wherein said ester is selected from the group consisting of diisopropyl sebacate, diisopropyl adipate, dioctyl maleate, dioctyl adipate, diethylhexyl naphthalate, and mixtures thereof.

5. A method of protecting skin from ultraviolet radiation comprising topically applying to the skin a composition comprising about 0.01 wt. % to about 50 wt. % of a compound of formula (I),

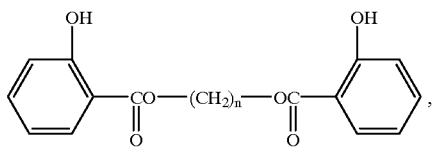

wherein n is an integer 3 to 12, in a cosmetically acceptable carrier.

6. The method of claim 8 wherein said composition further comprises a compound selected from the group consisting of a sunscreen agent, an ultraviolet light absorber, and mixtures thereof.

7. A method of treating skin conditions selected from the group consisting of acne, psoriasis, seborrheic dermatitis, dandruff, warts, corns, calluses, ringworm infection, wrinkling, yellowing, leatheriness, mottling, and hyperpigmentation, the method comprising topically applying to the skin a safe and effective amount of a compound of formula (I),

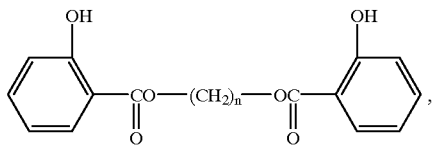

wherein n is an integer 3 to 12.

8. The method of claim 7 wherein the compound of formula (I) is in a cosmetically acceptable carrier.

9. The method of claim 7 wherein the compound of formula (I) is in a pharmaceutically acceptable carrier.

10. A method of increasing the sun protection factor of a sunscreen composition, compared to the sunscreen composition alone, comprising the step of adding about 0.01 wt. % to about 50 wt. % of a compound of formula (I),

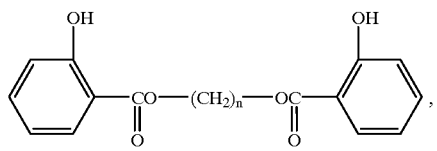

wherein n is an integer 3 to 12, to the sunscreen composition.

11. A method of providing a cosmetic composition with increased structure comprising the step of adding to said cosmetic composition about 0.01 wt. % to about 50 wt. %, based on the weight of the cosmetic composition, a compound of formula (I),

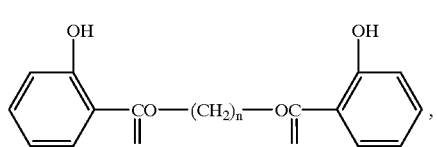

wherein n is an integer 3 to 12.

12. A cosmetic composition comprising a filler, a compression aide, a texture enhancer, a colorant, and a liquid binder, wherein about 0.01 wt. % to about 50 wt. % of the composition comprises a compound of the formula (I),

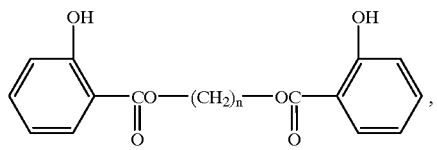

wherein n is an integer 3 to 12.

13. A cosmetic composition of claim 12 comprising the following formulation:

| Ingredient | % W/W |
| --- | --- |
| fillers | 30–70 |
| compression aides | 3–5.0 |
| texture enhancers | 10–40 |
| colorants | 2–10 |
| pearls | 0–10 |
| liquid binder | 3–8.0 | wherein about 0.01 wt. % to about 50 wt. % of the composition comprises a compound of formula (I).

14. A cosmetic composition of claim 12 comprising the following formulation:

| Ingredient | % W/W |
| --- | --- |
| fillers | 40–90 |
| compression aides | 0–2.5 |
| texture enhancers | 10–40 |
| colorants | 2–10 |
| pearls | 10–20 |
| liquid binder | 2–4.0 | wherein about 0.01 wt. % to about 50 wt. % of the composition comprises a compound of formula (I).

15. A cosmetic composition of claim 12 comprising the following formulation:

| Ingredient | % W/W |
|---|---|
| fillers | 40–80 |
| compression aides | 2–4.0 |
| texture enhancers | 10–30 |
| colorants | 1–10 |
| liquid binder | 4–8.0 | wherein about 0.01 wt. % to about 50 wt. % of the composition comprises a compound of formula (I).

16. A cosmetic composition of claim 12 comprising the following formulation:

| Ingredient | % W/W |
|---|---|
| fillers | 30–70 |
| compression aides | 2–5.0 |
| texture enhancers | 10–40 |
| colorants | 2–10 |
| pearls | 10–20 |
| liquid binder | 3–10 | wherein about 0.01 wt. % to about 50 wt. % of the composition comprises a compound of formula (I).

17. A cosmetic composition of claim 12 comprising the following formulation:

| Ingredient | % W/W |
|---|---|
| fillers | 30–60 |
| compression aides | 3–7.0 |
| texture enhancers | 3–30 |
| colorants | 1–25 |
| pearls | 0–50 |
| liquid binder | 3–15 | wherein about 0.01 wt. % to about 50 wt. % of the composition comprises a compound of formula (I).

18. An anhydrous foundation composition comprising the following formulation:

| Ingredient | % W/W |
|---|---|
| emollients | 30–60 |
| waxes | 5–10 |
| wetting agents | 0.50–1.00 |
| texturizing agents | 30–60 | wherein about 0.01 wt. % to about 50 wt. % of the composition comprises a compound of formula (I),

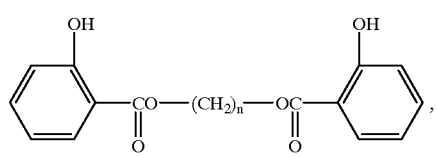

wherein n is an integer 3 to 12.

19. An anhydrous mascara composition comprising the following formulation:

| Ingredient | % W/W |
|---|---|
| volatile solvents | 40–60 |
| waxes | 10–20 |
| resins | 3–10 |
| gellants | 3–7 |
| colorants/pearls | 5–15 |
| functional fillers | 2–10 | wherein about 0.01 wt. % to about 20 wt. % of the composition comprises a compound of formula (I),

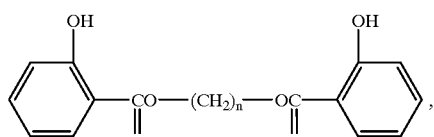

wherein n is an integer 3 to 12.

20. A cosmetic composition comprising a wax, a colorant, an emollient, and a filler, wherein about 0.01 wt. % to about 50 wt. % of the composition comprises a compound of the formula (I),

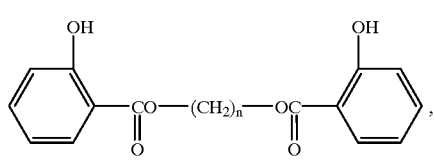

wherein n is an integer 3 to 12.

21. A cosmetic composition of claim 20 comprising the following formulation:

| Ingredient | % W/W |
|---|---|
| volatile solvents | 35–55 |
| waxes | 7–12 |
| emollients | 3–8 |
| gellants | 1.5–3.5 |
| colorants/pearls | 5–20 |
| fillers | 10–20 |
| functional fillers | 5–15 | wherein about 0.01 wt. % to about 20 wt. % of the composition comprises a compound of formula (I).

22. A cosmetic composition of claim 20 comprising the following formulation:

| Ingredient | % W/W |
|---|---|
| emollients | 50–70 |
| waxes | 10–15 |
| plasticizers | 2–5 |
| colorants | 0.5–3.0 |
| pearl | 1–4 |
| actives | 0–2 |
| fillers | 1–3 |
| fragrance | 0.05–0.10 |
| preservatives/antioxidates | about 0.5 | wherein about 0.01 wt. % to about 50 wt. % of the composition comprises a compound of formula (I).

23. A cosmetic composition of claim 22 wherein 60 to 85 wt. % of the composition consists of emollients, waxes, and one or more compounds of formula (I).

24. A cosmetic composition of claim 20 comprising the following formulation:

| Ingredient | % W/W |
| --- | --- |
| emollients | 40–55 |
| waxes | 8–13 |
| plasticizers | 2–4 |
| colorants | 3.0–8.0 |
| pearl | 3–6 |
| actives | 0–2 |
| fillers | 4–15 |
| fragrance | 0.05–0.10 |
| preservatives/antioxidates | about 0.5 | wherein about 0.01 wt. % to about 50 wt. % of the composition comprises a compound of formula (I).

25. A cosmetic composition of claim 20 comprising the following formulation:

| Ingredients | % W/W |
| --- | --- |
| solvents | 25–60 |
| emollients | 1–30 |
| waxes | 10–25 |
| fixatives | 1–10 |
| fillers | 1–15 |
| colorants/pearls | 1–15 |
| fragrance | 0.05–0.10 | wherein about 0.01 wt. % to about 50 wt. % of the composition comprises a compound of formula (I).

26. The composition of claim 5, wherein n is 6.

27. The method of claim 10, wherein n is 6.

28. A cosmetic composition comprising about 0.01 wt. % to about 50 wt. % of a compound of formula (I),

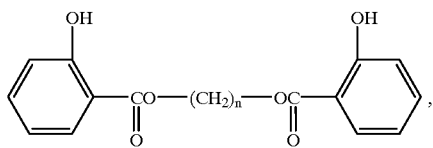
(I)

wherein n is an integer 3 to 12, and one or more cosmetically useful materials selected from the group consisting of a bulking agent, a colorant, an emollient, an emulsion stabilizer, a sunscreen agent, an ultraviolet light absorber, a wax, and combinations thereof.

29. The cosmetic composition of claim 27, wherein n is 6.

30. A method of providing a cosmetic composition with structure comprising the step of adding about 0.01 wt. % to about 50 wt. %, based on the total weight of the composition, of a compound of formula (I),

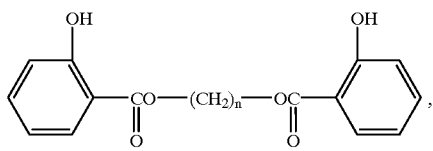
(I)

wherein n is an integer 3 to 12, to a cosmetically useful material selected from the group consisting of bulking agents, colorants, emollients, emulsion stabilizers, sunscreen agents, ultraviolet light absorbers, waxes, and combinations thereof.

31. A method of making a cosmetic composition comprising a wax and a cosmetically useful material, comprising the step of combining with said wax and said cosmetically useful material a compound of formula (I),

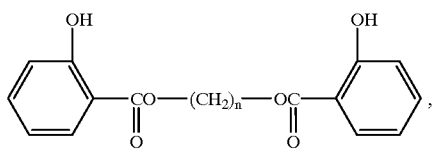
(I)

wherein n is an integer 3 to 12.

* * * * *

UNITED STATES PATENT AND TRADEMARK OFFICE
CERTIFICATE OF CORRECTION

PATENT NO. : 6,355,261 B1
DATED : March 12, 2002
INVENTOR(S) : Craig A. Bonda, Urvil B. Shah and Peter J. Marinelli It is certified that error appears in the above-identified patent and that said Letters Patent is hereby corrected as shown below:

Column 26,
Line 14, claim "27" should be claim -- 28 --.

Signed and Sealed this

Fifteenth Day of October, 2002

Attest:

Attesting Officer

JAMES E. ROGAN
Director of the United States Patent and Trademark Office